United States Patent [19]

Burks

[11] Patent Number: Plant 5,853

[45] Date of Patent: Jan. 13, 1987

[54] ROSE PLANT NAMED BURSTAR

[75] Inventor: Joe J. Burks, Tyler, Tex.

[73] Assignee: Co-Operative Rose Growers, Inc., Tyler, Tex.

[21] Appl. No.: 680,290

[22] Filed: Dec. 10, 1984

[51] Int. Cl.[4] ..... A01H 5/00

[52] U.S. Cl. ..... Plt./20

[58] Field of Search ..... Plt./20

*Primary Examiner*—R. E. Bagwill

*Attorney, Agent, or Firm*—Vincent G. Gioia

[57] ABSTRACT

A new hybrid tea rose variety which is a sport of the rose known as "Tropicana" (Super Star).

1 Drawing Figure

The present invention relates to a new and distinct variety of rose plant of the hybrid tea rose class, which is a sport (mutation) of the rose known as "Tropicana" which was discovered by me in Tyler, Tex. The denomination of this new rose is "Burstar".

Among the novel characteristics possessed by this new variety which distinguish it from the cultivar from which it sported and all other varieties of which I am aware are its flowers of much deeper color approaching the red end of the spectrum instead of the orange red of its parent cultivar. The new variety is also different in foliage, which is darker and larger; and plant habit which is more uniform. Asexual reproduction by budding of the new variety as performed in Clackamas County, Oreg., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "46A" is plate 46A of The Royal Horticultural Society Colour Chart.

Parentage: Sport (mutation) of the rose known as "Tropicana".
Class: Hybrid tea.

The following observations are made of specimens grown outdoors in Clackamas County, Oreg. during the month of September.

FLOWER

Blooming habit: Near continuous.

A. Bud:
- (1) *Size.*—Medium.
- (2) *Form.*—Ovoid.
- (3) *Color.*—As sepals fall, near 46A, then near 44B as petals unfurl.
- (4) *Sepals.*—Longer than bud, generally fancy, wooly inside, glaborous outside, with fine prickles, especially at base.

- (5) *Peduncle.*—Length — medium. Aspect — strong. Strength — erect. Color — near 143C with many fine prickles near 53A.

B. Bloom:
- (1) *Size.*—Average size when fully expanded — about 3½ inches.
- (2) *Borne.*—Singly, in late summer, basals with 3 to 5 blooms in conical sprays.
- (3) *Form.*—High centered at first becoming loose at maturity.
- (4) *Petalage.*—Number of petals under normal conditions — about 40.
- (5) *Color.*—(A): (during first two days). Basic coloration appears near 51D with brushed effect of 44B to 44C predominantly at the outer petal extremities. Color change to petal drop almost imperceptible.

C. Petals:
- (1) *Texture.*—Thick, very good substance.
- (2) *Appearance.*—Velvety inside, satiny outside, with faint veining.
- (3) *Form.*—Oval deltoid.
- (4) *Arrangement.*—Imbricated.
- (5) *Petaloids in center.*—Few, usually less than 5.
- (6) *Persistence.*—Drop off cleanly.
- (7) *Fragrance.*—Slight.
- (8) *Lasting quality.*—Very long lasting on plant and as cut flower.

REPRODUCTIVE ORGANS

A. Stamens, filaments and anthers:
- (1) *Arrangement.*—Regular arrangement, outer row longer and incurved.
- (2) *Color.*—Filaments near 43D, anthers 11B.

B. Pollen:
- *Color.*—Near 22A.

C. Styles: Uneven length, short due to gnarling near 46A, very slightly strigose.

D. Stigmas:
- *Color.*—Stigmatic surface, near 11D.

E. Hips:
- *Shape.*—Ovoid, sepals persist.
- *Size.*—⅜ to ½ inch.
- *Color.*—near 32A.
- *Do seeds protrude?.*—Yes.

PLANT

A. Form: Slightly spreading.

B. Growth: Very vigorous, uniform branching, with large basals appearing in late summer.

*Height attained.*—About 6 to 6½ feet.

C. Foliage: Compound 5 leaflets, many 3 leaflet leaves.

(1) *Size.*—Medium.

(2) *Quantity.*—Abundant, close internodes.

(3) *Color.*—New foliage: Upper side — near 187B. Under side — near 186A. Old foliage: Upper side — near 136A. Under side — near 138B.

(4) *Shape.*—Oval, acuminate, lower 2 leaflets smaller than upper 3.

(5) *Texture.*—Upper side is glossy and under side is textured, strong veining.

(6) *Edge.*—Serrated.

(7) *Serration.*—Simple.

(8) *Leaf stem.*—Color — near to 143A. Under side — near 143C with prominent prickles.

(9) *Stipules.*—Short, some bearding.

(10) *Resistance to disease.*—Blackspot — excellent. Mildew — excellent. Rust — excellent.

D. Wood:

(1) *New Wood.*—Color—near 143A overlayed 187C. Bark — smooth.

(2) *Old wood.*—Color — near 143C. Bark — smooth.

E. Thorns;

(1) *Thorns.*—Quantity (main stalk) — ordinary. On laterals from stalk — ordinary. Form — slender, recurved. Length — medium. Color — near 186B; near 165A when mature.

(2) *Prickles.*—Few on main stalks, profuse on laterals.

F. Winter hardiness: Winter hardy, no die back.

I claim:

1. A new and distinct variety of rose plant of the hybrid tea class which is a sport of the rose known as "Tropicana", substantially as shown and described, characterized particularly by flowers generally redder in coloring than orange red of "Tropicana" and foliage which is darker and larger and more uniform plant habit than "Tropicana".

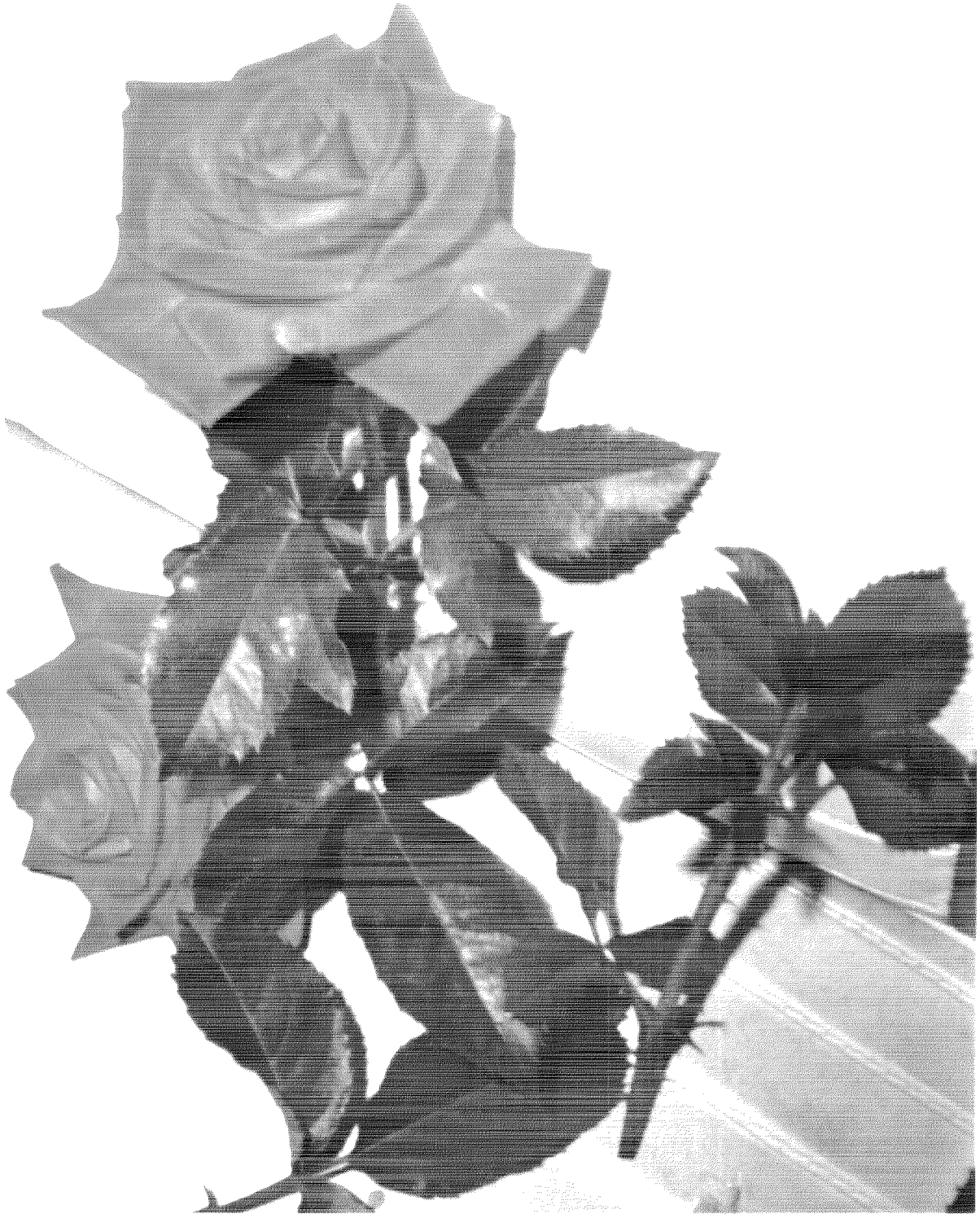

* * * * *